(12) United States Patent
Elvesjo et al.

(10) Patent No.: US 7,572,008 B2
(45) Date of Patent: Aug. 11, 2009

(54) METHOD AND INSTALLATION FOR DETECTING AND FOLLOWING AN EYE AND THE GAZE DIRECTION THEREOF

(75) Inventors: John Elvesjo, Stockholm (SE); Marten Skogo, Stockholm (SE); Gunnar Elvers, Lidingo (SE)

(73) Assignee: Tobii Technology AB, Stockholm (SE)

( * ) Notice: Subject to any disclaimer, the term of this patent is extended or adjusted under 35 U.S.C. 154(b) by 314 days.

(21) Appl. No.: 10/535,227

(22) PCT Filed: Nov. 21, 2003

(86) PCT No.: PCT/SE03/01813

§ 371 (c)(1),
(2), (4) Date: Apr. 6, 2006

(87) PCT Pub. No.: WO2004/045399

PCT Pub. Date: Jun. 3, 2004

(65) Prior Publication Data

US 2006/0238707 A1    Oct. 26, 2006

(30) Foreign Application Priority Data

Nov. 21, 2002   (SE)   .................................... 0203457

(51) Int. Cl.
*A61B 3/14*   (2006.01)
*G03B 17/00*   (2006.01)

(52) U.S. Cl. ........................................ 351/206; 396/51
(58) Field of Classification Search ................ 351/205, 351/206, 208; 396/51
See application file for complete search history.

(56) References Cited

U.S. PATENT DOCUMENTS 5,218,387 A * 6/1993 Ueno et al. .................. 351/210

(Continued)

FOREIGN PATENT DOCUMENTS

DE    19731301 A1    1/1999

(Continued)

OTHER PUBLICATIONS

International Search Report for PCT/SE2003/001813 mailed Mar. 4, 2004.

(Continued)

*Primary Examiner*—Ricky L Mack
*Assistant Examiner*—James R Greece
(74) *Attorney, Agent, or Firm*—Nixon & Vanderhye P.C.

(57) ABSTRACT

When detecting the position and gaze direction of eyes, a photo sensor (1) and light sources (2, 3) placed around a display (1) and a calculation and control unit (6) are used. One of the light sources is placed around the sensor and includes inner and outer elements (3'; 3"). When only the inner elements are illuminated, a strong bright eye effect in a captured image is obtained, this resulting in a simple detection of the pupils and thereby a safe determination of gaze direction. When only the outer elements and the outer light sources (2) are illuminated, a determination of the distance of the eye from the photo sensor is made. After it has been possible to determine the pupils in an image, in the following captured images only those areas around the pupils are evaluated where the images of the eyes are located. Which one of the eyes that is the left eye and the right eye can be determined by following the images of the eyes and evaluating the positions thereof in successively captured images.

12 Claims, 4 Drawing Sheets

U.S. PATENT DOCUMENTS

| | | | |
|---|---|---|---|
| 5,293,427 A | * | 3/1994 | Ueno et al. ................. 382/103 |
| 5,638,176 A | | 6/1997 | Hobbs |
| 6,152,563 A | * | 11/2000 | Hutchinson et al. ......... 351/209 |
| 6,421,064 B1 | * | 7/2002 | Lemelson et al. ........... 345/688 |

OTHER PUBLICATIONS

European Communication pursuant to Article 96(2) EPC for EP 03 776 116.0 dated May 8, 2006.

* cited by examiner

Let d be the distance between the reflections of the two light sources in the two-dimensional picture captured by the photosensor $d \sim \theta$ $h \approx x\theta$ $h = 2r \sin(\frac{\varphi}{2})$ $\varphi = \varphi' - \frac{\theta}{2} \approx \varphi'$ $\varphi' \approx \arctan(\frac{a}{x})$ $d \sim \frac{r}{x} \sin[\frac{1}{2} \arctan(\frac{a}{x})]$ ● Non-illuminated diode
○ Illuminated diode Image of an eye when the illumination is in light setting position (i)

Boundary lines obtained from image of Fig. 4a

Image of an eye when the illumination is in light setting position (ii)

Boundary lines obtained from image of Fig. 5a $d(n)$ = maximum allowable distance for $n$ iterations according to velocity limit for movement of eye [pixels]

$d_{max}$ = maximum possible distance in picture for $n$ iterations [pixels]

$n_{max}$ = largest number of iterations considered

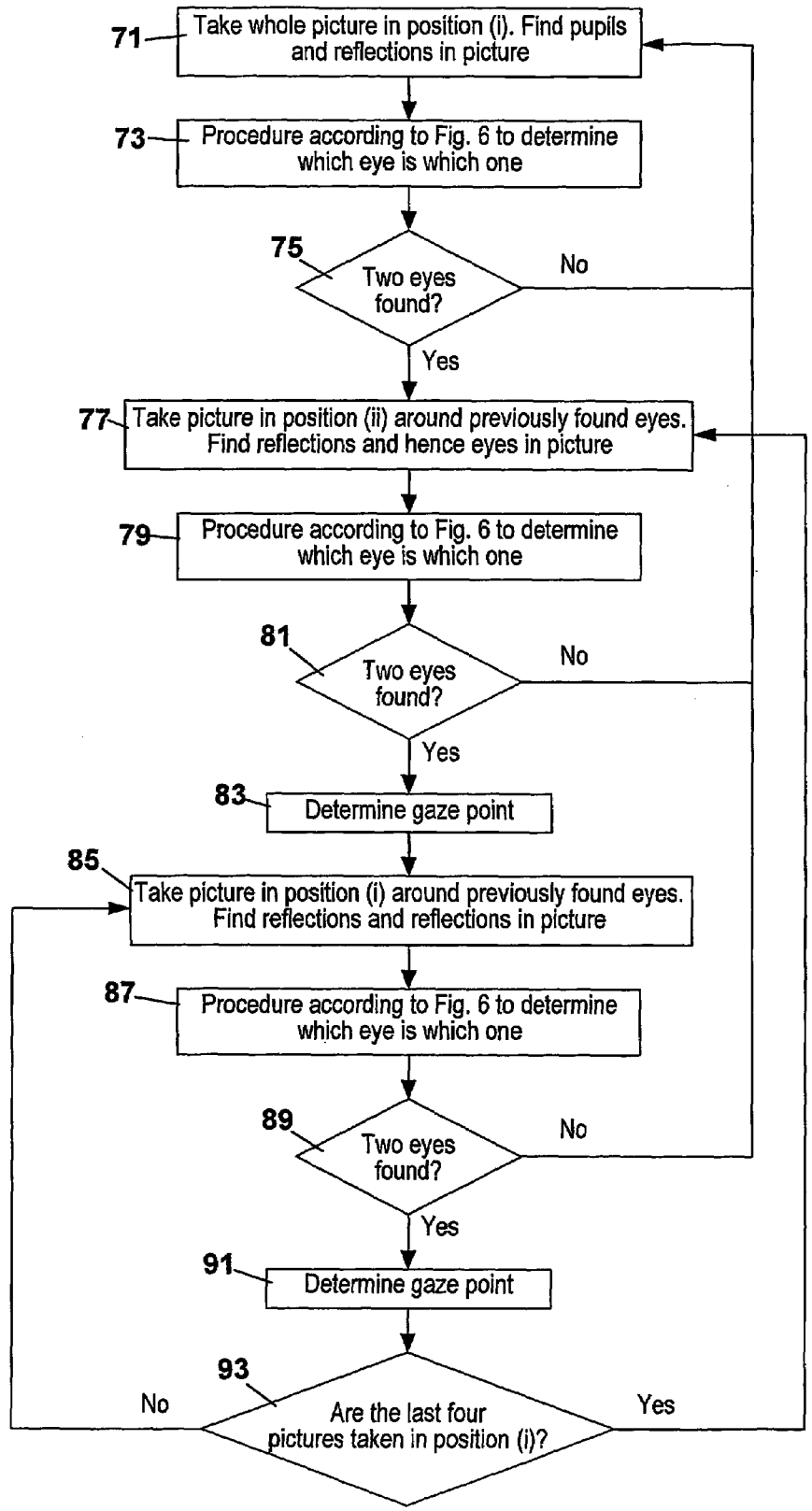

ND INSTALLATION FOR
METHOD AND INSTALLATION FOR DETECTING AND FOLLOWING AN EYE AND THE GAZE DIRECTION THEREOF

This application is the US national phase of international application PCT/SE2003/001813 filed 21 Nov. 2003 which designated the U.S. and claims priority of SE 0203457-7, filed 21 Nov. 2002, the entire contents of each of which are hereby incorporated by reference.

RELATED APPLICATION

This application claims priority and benefit from Swedish patent application No. 0203457-7, filed Nov. 21, 2002, the entire teachings of which are incorporated herein by reference.

TECHNICAL FIELD

The present invention relates a method and an installation for detecting and tracking eyes and gaze angles/directions. Such a system can for example be used for observing or determining the position on a monitor or display at which a computer user is looking.

BACKGROUND

Monitoring or tracking eye movements and gaze points can be used in many different contexts. Information about the position at which a person is looking can be used for analyzing the behavior and consciousness of the person. It can be used both for evaluating the object at which the person is looking and for evaluating the respective person. The fields of use are many and thereamong studies on the usability of software and different types of interfaces, evaluations of home pages, advertising and advertisements, means for educating pilots in simulator surroundings, research in psychology, behavior science and human perception and diagnosis of various types of visual faults and illnesses can be mentioned.

In addition to these applications also interactive applications exist which employ information about the place at which a person is looking in order to respond or react in different ways. A physically disabled person can for example interact with a computer by the procedure that those objects on the monitor of the computer at which he is looking are activated. In an arcade game the adventure experience of the game can be very much enhanced by the procedure that those objects at which a person is looking are made to be centered in the image or by the procedure that the person is allowed to direct a weapon using her/his eyes. In the same way the advertising or display for Christmas in a shop window can react to the fact that a person is looking at it. Interfaces for for example a computer could utilize continuous information about the position at which a user is looking to be better capable of displaying the object in which a user is interested and of adapting in an intelligent way to different behaviors of the user. A motorcar that receives information about the position at which the driver is looking could issue an alarm in the case where the driver is tired, distracted or intoxicated. Military applications for directing weapons or for steering vehicles using eye movements have also been developed. These are only a small number of the fields of use that can be of interest for an installation that can detect and track eyes and gaze angles.

Many different technologies exist that can be used for tracking an eye and the gaze angle thereof. A first technology is to use a photosensor and a light source, the light of which is reflected from the cornea and from the lens of an eye and thereby causes four different reflections. The reflection thereof having the strongest light intensity is the outer cornea reflection or glint, also called the first Purkinje reflection. Thereafter the second, the third and fourth Purkinje reflections follow which correspond to reflections in the inner surface of the cornea, the outer surface of the lens and the inner surface of the lens. The first and fourth Purkinje-reflections are located in the same focal plane and the relationship of the positions of these two reflections varies with rotation of the eye.

A second technology for tracking an eye and the gaze angle thereof is to detect, using some type of photosensor, the boundary line between the white or sclera and the iris of an eye. A third technology is to detect the face of person using a camera and to indirectly deduce, by observing how the eyes move in relation to the face, the direction in which the person is looking. A fourth technology is to use that the cornea and the retina have different electrical potentials for measuring rotation of an eye. A fifth technology is to use a contact lens fitted with suitable devices to be capable of measuring how the contact lens and hence also the eye rotates. A sixth technology is to measure, using a photosensor, the ellipticity of the pupil or of the iris when the eye rotates. A seventh technology is to use a diode and two or more optical transistors mounted in a pair of spectacles. When the light from the diode is reflected from the cornea and then hits an optical transistor the signals provided by the transistor will vary in accordance with the travel distance of the light from the diode via the cornea and to the transistor. An eight technology is to use a photosensor to detect the reflection of a light source from the cornea and then to observe how the position thereof is related to the center of the pupil or iris. The pupil can in this case be made more easily observable by using illumination devices mounted close to the photosensor illuminating the retina of the eye and thereby causing a bright eye effect or by illuminating the eye so that the iris is made bright whereas the pupil remains dark.

In U.S. Pat. No. 5,861,940 a system for detecting eyes and for tracking gaze angles is disclosed. The system includes light sources comprising an IR-laser 2 that is provided with a suitable optical system and issues a convergent light beam with a focus in front of the eye and two IR-lasers or IR-diodes 9, 10 that alternatingly emit divergent light beams. By detecting the reflection from the retina using a position sensitive detector information about the position of the eye is obtained. By detecting the reflections of a plurality of light sources from the cornea the distance of the eye from the video camera is determined. The latter two IR-lasers are placed at the bottom edge of a computer monitor 1. Other systems are disclosed in U.S. Pat. Nos. 6,079,829, 6,152,563 and 6,246,779.

In automatic systems that employ a video camera it can be difficult to determine the positions in a captured picture, where reflections of light sources from the eyes of a user are located. This depends among other things on the fact the user can move her/his head, displace it laterally or to places at a smaller or larger distance of the camera. The automatic system can contain complex image processing and image recognition routines for determining those areas where images of eyes are located. Hence there is a need for methods for facilitating such determinations of areas in a captured picture in which reflections and images of eyes are located. Furthermore, in determining the point of regard on a surface such as a monitor, always the distance between the eyes of the user and the monitor must be determined and thus efficient methods for such a determination are required.

SUMMARY OF THE INVENTION

It is an object of the invention to provide an efficient method and an efficient installation for detecting and tracking eyes and gaze angles/directions.

In a method and in a device for detecting eyes and gaze angles/directions a photosensor such as a CCD-unit or CMOS-unit provided with a suitable optical system or a video camera, one or more light sources and a calculation and control unit are used. To determine the position on for example a monitor at which a person is looking the position of the eyes of the person, both in a depth direction and in lateral directions, as seen from the monitor, and the direction in which the eye is looking, must be known. If only the angle and the position in two dimensions are known, a parallax distortion will evolve when the eye moves in the depth direction. This parallax distortion is often significantly larger than what is acceptable in many applications.

To determine the position of an eye, i.e. the position thereof in relation to a photosensor or a monitor, the eye is illuminated using two or more light sources arranged at a distance of each other. The images of the reflections of these light sources from the person's cornea on to the photosensor will then depend on the place in the field of vision of the photosensor at which the person is located. The images of the reflections on the photosensor provide all the information required to exactly determine the place where the person is located in the field of vision of the photosensor. If it is assumed that the cornea of the eye is spherical this function is unambiguously defined and is invertible already in the case where the number of light sources is as small as two, but also using more advanced assumptions a good accuracy and reliability in the determination of the place where the eyes are located are obtained by evaluating the whole pattern that is formed from reflections of a plurality of light sources, i.e. the positions of the reflections in relation to each other and in the whole picture. In a simple case only the size of the pattern and the position thereof in the captured picture are determined.

Thus, in the method a photosensor is used for creating a two-dimensional picture of the reality and generally one or more light sources. The light source/light sources illuminate possible eyes within the visual field of the photosensor so that diffusely reflecting surfaces become more easily observable to the photosensor and so that light from the light source/light sources reaching corneas causes reflections which by the photosensor are experienced as discrete bright points.

The two-dimensional picture created by the photosensor is analyzed using complex image processing to determine the position in the picture where possible eyes and reflections of light are located. This information is then used to determine where eyes are located and/or in which directions they are looking, which in turn can be used for for example determining the position on a monitor at which a computer user is looking.

In the two-dimensional picture pupils and/or irises are searched for. The image of the pupil can be made more easily observable by illuminating it by one or more light sources. The light source/light sources can be placed at a distance from the optical system that focuses the two-dimensional picture on the photosensor. It results in that only a small portion of the illuminating light will enter the eye and hence that the pupil will appear as darker than the surrounding face. In that way the boundary line between the pupil and the iris can be more easily detected than in the case where no illumination is used.

An alternative to the illumination mentioned above comprises that the light source/light sources are placed very close to or on the optical system that focuses the two-dimensional picture on the photosensor. The diffused field of the light source/light sources then corresponds to the field of vision of the photosensor, and to an eye that is located within the field of vision of the photosensor the point on the retina that is illuminated by the light source/light sources will be the same or at least partly the same point that is imaged on the photosensor. It results in that the pupil appears to be brighter than the surroundings thereof. The phenomenon is the same one that results in that eyes on photographs can appear to have a reddish color.

To achieve the possibly strongest bright eye effect the light source/light sources are mounted as close as possible to the visual axis of the photosensor without interfering with the field of vision of the sensor. The portion of the retina of an eye that the photosensor is seeing then largely coincides with the portion of the retina that is illuminated by the light source/light sources. Provided that the light source/light sources must be placed in front of the optical system that focuses the picture on the photosensor, a light source having a central hole of the same shape as the photosensor is a good way of arranging the light source/light sources as close to the visual axis of the photosensor without interfering with the visual field thereof. The larger distance from the optical system the light source is placed the larger the hole must be in order not to interfere with the visual field of the photosensor. Therefore it is desirable to be capable of placing the light source as close to the optical system as possible in the case where a bright eye effect is aimed at.

Using the bright eye effect for determining the direction of eyes, at the same time as the positions of eyes are determined using a plurality of light sources that are reflected, can cause problems. The bright eye effect is achieved by using an illumination device/light source that is placed as close to the photosensor as possible. An illumination device placed at a distance from this light source will illuminate everything in addition to the pupil of the eye that is located within the visual field of the photosensor and hence reduce the contrast between the pupil and the iris in pictures captured by the photosensor. In addition there is a high probability that the reflection of this additional light source in the picture will be located precisely at the boundary line between the pupil and iris which even more makes the search for this transition difficult. As seen from the opposite perspective, that the position of the eye is to be determined, the bright eye effect that is used to bring out or enhance the pupil results in that the contrast of the transition region in the picture between the pupil and a reflection from the cornea in front of the pupil becomes lower compared to the case in which the pupil had not been illuminated using the bright eye effect. Thus, there is a risk that it could be difficult to observe reflections located in images of the illuminated pupil. To avoid these problems two light settings, one for determining the direction and another for determining the position, can be alternated with each other so that only one is active for each captured picture. This implies that both the direction and the position cannot be determined from each picture but on the other hand it increases the robustness of the system.

If the light source/light sources instead is/are placed at a distance from the optical axis of the photosensor a dark pupil is obtained whereas the surrounding face becomes brighter the stronger the light sources/light sources radiates/radiate. This light setting is preferred in the case where the iris to be found and it also has the advantage that the contrast between the pupil and the iris is not made lower or worse by diffuse light from the surroundings as is the case for a system based on the bright eye effect.

In order not to disturb the person that is illuminated by the light source/light sources the light source/light sources can be used to emit light having wavelengths that are not visible to the human eye but that can be detected by the photosensor. For example, light in NIR-range, (NIR=Near Infrared) can be used, i.e. light having wavelengths somewhat longer than what can be perceived by a human eye. Such light can be detected by most photosensors designed to detect visible light.

The photosensor used can advantageously be a high resolving type/high resolution type. It results in the fact that a large amount of data is obtained when the whole photosensor is exposed. In order to reduce the resources used in processing data from only a given area of interest (AOI) can be selected to be processed. Thus, to reduce the load on the communication link between the photosensor and the calculation unit the calculation unit can select to only ask the photosensor to provide those data that come from the current AOI. In that way both calculation and communication resources can be released for other purposes. To be capable of selecting a proper AOI for an exposing of the photosensor advantageously information about the positions where the eye has been located in the directly preceding pictures is used.

The greatest advantage is obtained if as large portion of unnecessary picture information as possible is discarded as early as possible in the procedure. If the photosensor is made to only expose or forward a portion of the information from the sensor surface to the evaluation unit new possibilities evolve that previously were not possible. In that way photosensors having a very high resolution can be used without causing that the procedure operates slower. Instead of camera interfaces that are advanced, difficult to initiate and costly, standardized PC-buses can be used to obtain a sufficient transmission rate from the photosensor to the evaluation unit. Also the very exposing and the reading out of the photosensor data in many cases require a shorter time period if only a selected portion of the sensor is exposed. It results in that a larger velocity can be obtained in the determination of the gaze point for the eye that is tracked. This is valuable in many applications such as for example in psychological studies.

Additional objects and advantages of the invention will be set forth in the description which follows, and in part will be obvious from the description, or may be learned by practice of the invention. The objects and advantages of the invention may be realized and obtained by means of the methods, processes, instrumentalities and combinations particularly pointed out in the appended claims.

BRIEF DESCRIPTION OF THE DRAWINGS

While the novel features of the invention are set forth with particularly in the appended claims, a complete understanding of the invention, both as to organization and content, and of the above and other features thereof may be gained from and the invention will be better appreciated from a consideration of the following detailed description of non-limiting embodiments presented hereinbelow with reference to the accompanying drawings, in which:

FIG. 7 is a flow diagram of the total procedure that is performed in an installation for determining the gaze direction and the position of an eye.

DETAILED DESCRIPTION

Figure 1:
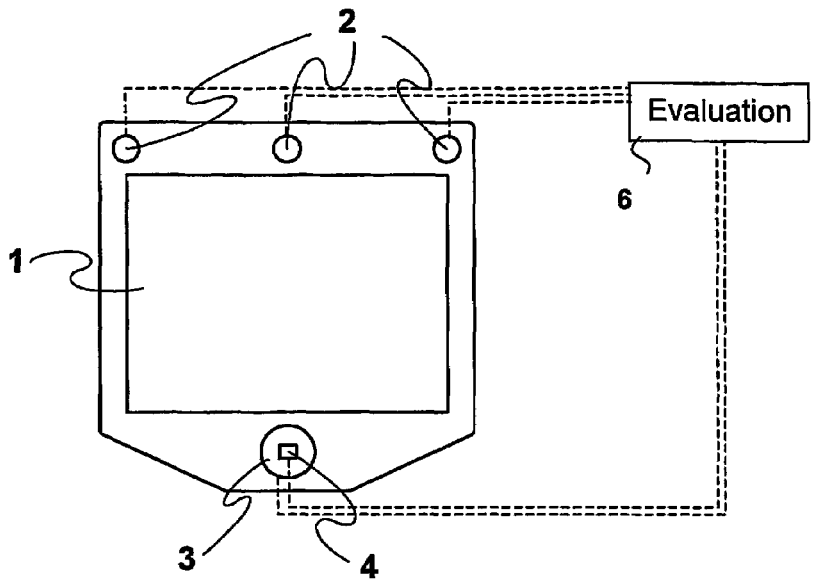
FIG. 1 is a schematic picture from the front of an embodiment of an installation for detecting and tracking eyes and gaze angles.

In FIG. 1 an installation for determining the point on a monitor 1 at which a computer user is looking/gazing is shown. The determination is performed by tracking the eyes of the user and in particular by determining the gaze angles of the eyes and the distance of the eyes from the monitor. The installation includes the monitor 1, three identical light sources 2 mounted along a straight line at the upper edge of the monitor 1, a photosensor 4 placed at the center of the bottom edge of the monitor and provided with a suitable optical system, not shown, that is located in front of the photosensor for both filtering away undesired light and for focusing a picture on the light sensitive surface of the photosensor, and a light source 3 placed coaxially with the optical axis of the photosensor, i.e. located around, at all sides of, the light sensitive surface of the photosensor. The light sensitive surface can, as shown, have a rectangular shape. The coaxial light source 1 includes, see FIGS. 3a and 3b, a plurality of light emitting elements 3', 3" arranged in two groups, an first inner group and a second outer group. In the inner group the light emitting elements 3' are placed close to the edges or sides of the light sensitive surface. In the embodiment shown including a rectangular light sensitive area three elements are placed at each long side of the rectangular shape and two elements at each short side thereof. In the outer group the light emitting elements 3" are placed at a larger distance of the light sensitive area, outside the elements in the inner group as seen from the center of the light sensitive are. In the embodiment shown there are as many elements in the outer group as in the inner group and each element in the outer group is placed between two elements in the inner group, as seen from the center of the rectangular light sensitive area.

In a practical embodiment of the installation according to FIG. 1 the three identical light sources 2 each comprised seven NIR-diodes, HSDL 4230, including six diodes arranged symmetrically around a center diode. The same types of diodes are used as the light emitting elements 3', 3" in the illumination unit 3 designed according to FIGS. 3a and 3b.

In addition to these components only a coordinating calculation and control unit is provided, indicated at 6, for performing the required control and evaluation associated therewith and calculations. Thus, the calculation and control unit controls switching the light sources on and off. Furthermore it performs processing of images captured by the photosensor 4, in particular determination of boundary lines, i.e. lines between fields in the pictures that have different grey scale intensities or colors. In the image of an eye among other things the boundary line is determined that delimits the pupil and therefrom the center of the pupil is obtained. The latter can be made by for example adapting a circle or ellipse to the boundary line that has been decided to delimit the pupil. The calculation and control unit 6 can also control, as will be described hereinafter, the data output from the photosensor 4, i.e. determine the picture elements in a captured image for which information is to be forwarded from the photosensor to the calculation and control unit.

Figure 3A:
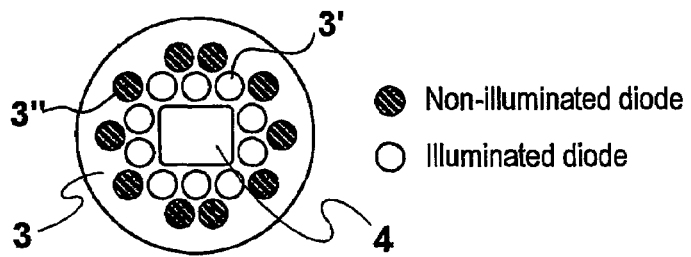
FIGS. 3a and 3b are schematic pictures from the front of an example of an embodiment of an illumination device that is coaxial with the visual field of the photosensor for achieving a bright eye effect when different diodes are switched on and off.
Figure 3B:
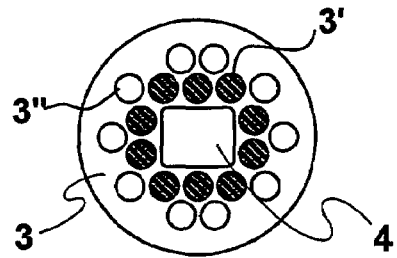

In FIGS. 3a and 3b it is seen how the elements in the light source 3 are placed around the photosensor 4 to be capable of illuminating the eye in two different ways, by switching the light emitting elements of the inner or outer group on and off. One light setting position which is seen in FIG. 3 and in which only the elements in the inner group are switched on causes an easy observable bright eye effect of the pupils that are detected by the photosensor whereas the other setting position which is shown in FIG. 3b and in which only the elements in the outer group are switched on causes reflections from corneas without causing any easy observable bright eye effect.

When the installation of FIG. 1 is operating, it alternates between two light setting positions. Setting position (i) is provided for determining the direction in which the user is looking. In light setting position (ii) the distance from the eyes of the user to the photosensor is determined. In both light setting positions also information about the place at which the eye or eyes of the user is located as seen in the two-dimensional coordinate system of the photosensor is obtained.

When the installation is in light setting position (i) the inner elements 3' of the light source 3 that is arranged coaxially with the field of vision of the photosensor 4 are switched on in the setting position that is shown in FIG. 3a and gives a strong bright eye effect for all pupils within the field of vision of the photosensor. In this light setting position all the three light sources 2 placed above the monitor 1 are switched off, i.e. only the elements in the inner group are switched on. The image of a pupil within the visual field of the photosensor 2 will then look as appears from FIG. 4a in which the pupil 5, compare FIG. 4b, is illuminated due to the bright eye effect and the reflection of the light source 3 from the cornea is seen as a point-shaped reflection 3'a. The captured image is analyzed by the calculation unit 6 and boundary lines according to FIG. 4b are determined. In the picture captured for the bright eye effect there is a particularly large contrast between the image fields that correspond to the pupil and the iris, compare the picture of FIG. 5a which is captured using a different illumination, and therefore the boundary line between these two fields can be calculated with a good accuracy. This accurately determined boundary line delimits the pupil and therefrom the center of the pupil can then be determined, consequently also with a good accuracy. In the determination of the center, as has been mentioned above, adaptation of an ellipse to the boundary line can be used, which is particularly important in the case where the pupil is only partly visible in the picture. Furthermore, in the picture the position of a reflection 3'a and particularly the center of the reflection are determined. Finally the vector from the center of the reflection 3'a to the center of the pupil 5 is calculated.

To determine the gaze direction, i.e. the direction in which the user is looking, the vector determined according to the description above is used. The direction of this vector indicates the direction in which the user is looking as taken from the optical axis of the camera and the magnitude of the vector indicates the angle in which the user looks, also taken in relation to the optical axis of the camera. Furthermore, the center of the reflection 3'a provides information about the position of the eye of the user as seen in two dimensions.

Figure 4B:
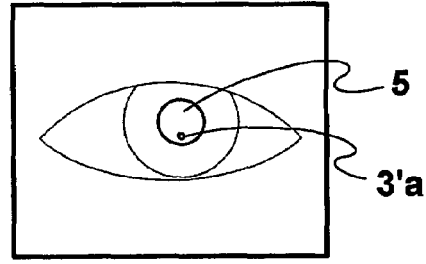
FIG. 4b is a picture obtained using boundary line analysis of the picture of FIG. 4a, FIG. 5a is a picture of an eye similar to FIG. 4a but illuminated for making it possible to determine the distance of the eye from the photosensor.
Figure 5A:
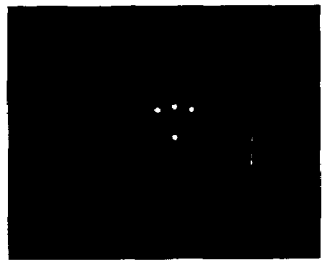
FIG. 5b is a picture obtained using boundary line analysis of the picture of FIG. 5a, FIG. 6 is a flow diagram illustrating steps in processing information about found eyes in a two-dimensional picture for determining which eye is the right or the left one of a user.
Figure 5B:
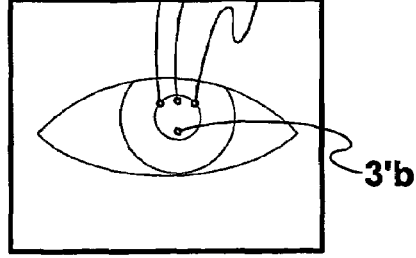

When the system is in light setting position (ii), the elements 3" in the outer group in the light source 3 that is coaxial with the visual field of the photosensor are switched in the light setting position according to FIG. 3b that does not result in any clearly observable bright eye effect. At the same time the three light sources 2 placed at the upper edge of the monitor are switched on in this light setting position. FIG. 5a illustrates how an eye can be imaged on to the photosensor 4 in this setting position with a relatively low contrast between the image fields that correspond to different portions of the eye. Also this picture is analyzed to obtain boundary lines, as is illustrated in FIG. 5b, and the accuracy of the determined boundary lines of fields corresponding to different portions of the eye can be lower than that of the line delimiting the pupil according to FIG. 4b. However, in the picture according to FIG. 5b the different reflections appear very clearly. At 3'b, see the analyzed picture in FIG. 5b, thus the reflection of the light source 3, that is switched on according to the case appearing from FIG. 3b, from the cornea is illustrated and at 2' the reflections of the light sources 2 placed at the upper edge of the monitor from the cornea are shown. The positions of and the distances between the different reflections are determined in the picture and this determination can then be made with a good accuracy. The pattern of the four reflections, i.e. primarily the positions of the different reflections in relation to each other, is evaluated to determine the distance of the eye from the photosensor 4. In particular the size of the pattern that is formed by the four reflections at 2', 3'b is dependent on the distance of the eye from the photosensor. The longer from the photosensor the eye is located, the smaller are the dimensions of the pattern. In that way a measure of the distance at which the monitor 1 is located from the eye of the user is obtained. Also in this case information about the place where the eye of the user is located in two dimensions is obtained from the reflection of the coaxial light source 3 at 3'b.

Thus, when the system of FIG. 1 is in operation, it alternates between light setting position (i) and light setting position (ii). It requires information from these two light setting positions to be capable of indicating the position on a monitor at which a user is looking. In light setting position (i) the gaze direction of the user is detected and in light setting position (ii) the position of the user is detected. For a computer user, eye movements are usually significantly much more rapid than movements of the head. This means that it is more important to have recently updated information about the gaze angle of the user than about the position of the user in the depth direction from the photosensor 4 to obtain a good accuracy in the determination of the point on the computer monitor on which the user is looking. Experiments indicate that in the case where four pictures captured in light setting position (i) are analyzed for each picture in light setting position (ii) a system having a good accuracy is obtained. For determining the gaze point information from the last picture taken in light setting position (i) and from the last picture captured in light setting position (ii) is always used.

Figure 2:
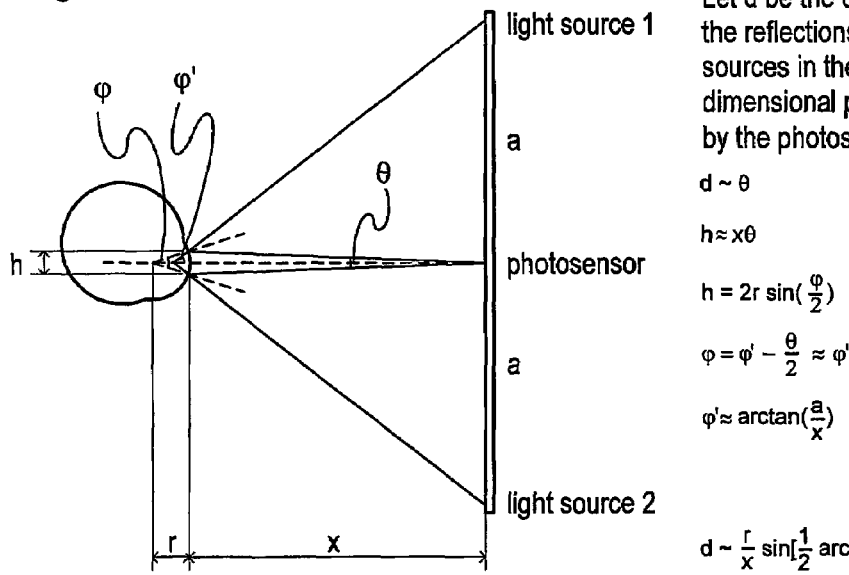
FIG. 2 is a schematic diagram of the dependence, in a two-dimensional picture captured by a photosensor, of the distance between two light sources reflected from a cornea on the distance of the cornea from the photosensor.

In FIG. 2 is schematically illustrated how the distance between images of reflections of two light sources depends on the distance of the reflecting surface from the light sources and the detector which are assumed to be located in the same plane. The distance between the reflecting surface and the plane through the light sources is roughly inversely proportional to the square root of the distance between the images. Such a relationship or a somewhat more exact relationship, as appears from FIG. 2, can be used together with absolute values obtained in an individual calibration of the installation for each user to give a sufficiently accurate distance determination for for example control of a cursor on the monitor when the head of the user is moving.

The photosensor used in the installation described above is of high resolution type. In that way the user can be allowed to have a greater mobility of her/his head without producing a degraded accuracy. To reduce the load on the calculation unit and increase the sampling velocity of the system data from the photosensor are not more than then necessarily used. The calculation unit uses information about the positions where eyes have been found in previous pictures to select the portion of the light sensitive surface of the photosensor that is to be exposed before each new picture to be taken or to be used in each new picture and controls the photosensor in accordance therewith. If the user's eyes are found in the preceding picture only a small portion of the picture elements of the light sensitive surface of the photosensor is used. Only in the case where no eyes have been found data from all picture elements of the light sensitive surface of the photosensor are used or in any case data representing the whole picture surface, obtained for example by a down sampling operation of data for the total picture area. In that way a system is obtained that is relatively slow in detecting eyes and the distance of eyes in the depth direction but that can be made to track eyes and in particular the gaze direction with a high velocity after the eyes have been found.

Figure 4A:
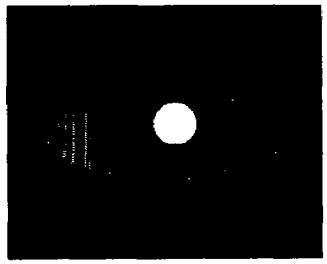
FIG. 4a is a picture of an eye captured using a photosensor and illuminated in order to make it possible to determine the gaze angle of the eye and the place on which it is located in the two-dimensional coordinate system of the photosensor.

An eye has unique physical characteristics which together with the position of the eye and the gaze direction control how a picture captured as illustrated in FIG. 4a or 5a will appear. To be capable of determining the position at which a person is looking from the data that can be obtained from these pictures the system can be individually calibrated, if required, for the person that is sitting in front of the monitor. In addition the system has to know which eye is which one, i.e. if the boundary lines calculated according to FIGS. 4b and 5b are associated with the left or right eye of the user.

When the two eyes of a user are visible to the photosensor 4 it is easy to tell which eye that is the left eye and which one is the right eye but in the case where only one eye has been found another method is required to determine which eye it is. Such a method will now be described and the different steps therein are also illustrated by the flow diagram of FIG. 6. The first factor having influence is the motion velocity of the eyes of the user. There is an upper limit for the velocity with which an eye can move. It results in that if there is a known eye in a given position in a previous picture this eye cannot have moved more than a definite distance after the previous picture was captured. Thus, if the distance is too large between the previously known eye and the eye now found, the eye now found is an eye different from that which was previously detected. Even if the previously known eye was the only known eye at that time there must have been an area within which the other eye should have been located. The distance between the eyes of a user can in this way be used to judge whether the eye that was not known can have moved to the position where the new eye was found. If the distance is sufficiently small for only one of the eyes of the user the found eye must be the same one as this eye.

If said criteria do not give information about which eye has been found another factor exists which can be considered. This factor is how close to the edge of the photosensor the eye is located. If the eye is located so close to the outer edge of the photosensor that the other eye should be located outside the visual field of the sensor, if it was located on the outer side of the found eye, it is true that either this must be true or that the other eye is located within the gaze angle of the photosensor but is concealed—probably due to the fact that the user has closed it. In this case it can be allowed that the system will guess that the found eye is the eye that implies that the other eye is outside the field of vision of the photosensor. After the system has guessed which eye has been found a lower confidence level is set for the data that are forwarded from the system to show that these data are not secure.

Figure 6:
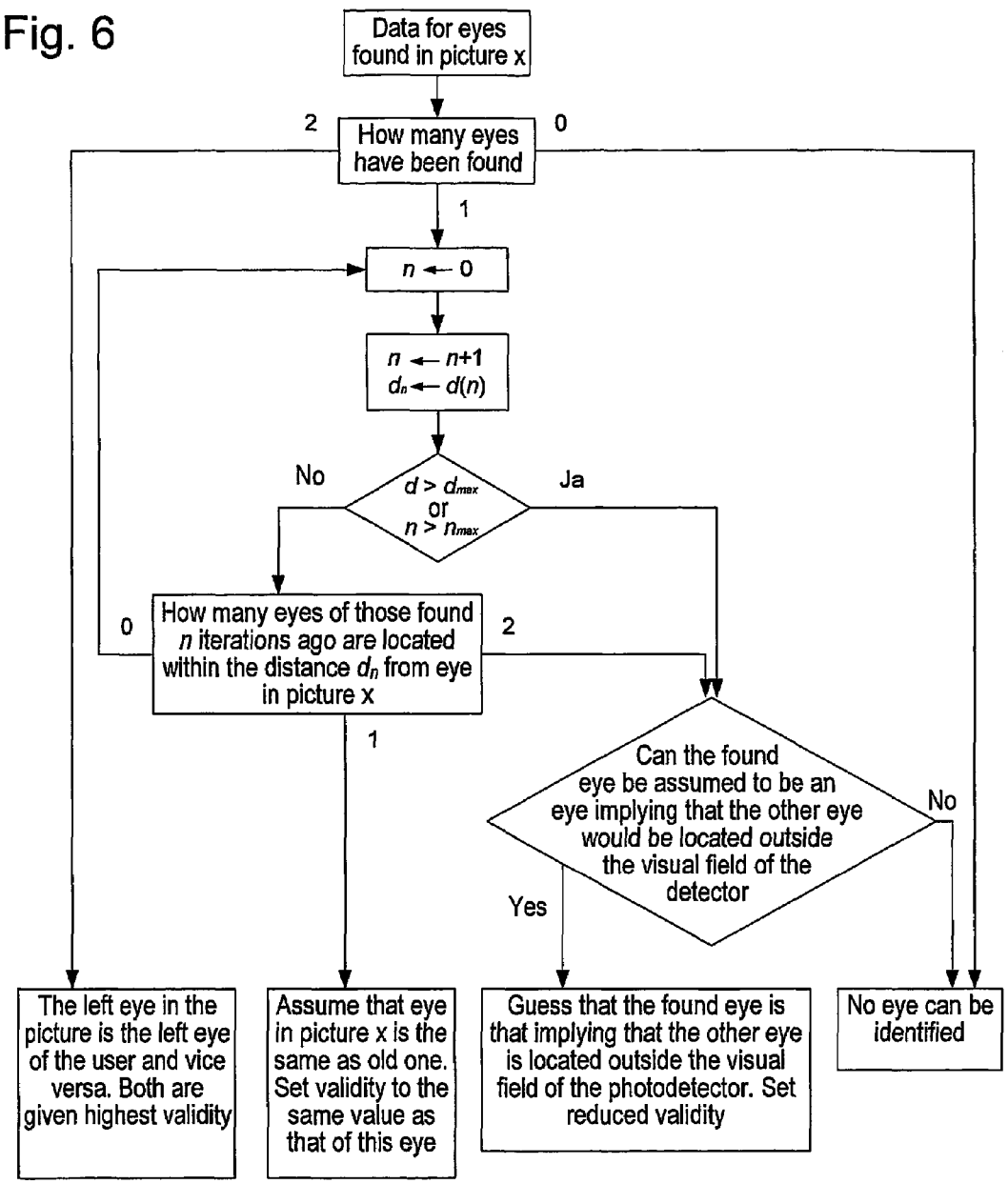

In FIG. 7 a flow diagram of the different steps executed in determining and tracking the eyes and gaze direction of a person is shown. In a first step 71 a picture is captured with illumination in light setting position (i), i.e. when only the elements 3' are switched on. In the picture pupils are determined, i.e. their boundary lines, and reflections of the light source. In the next block 73 the procedure according to FIG. 6 is executed to determine which eye is which one. In step 75 it is then decided whether two eyes have been found in the picture. If it is true, a block 77 is executed in which a picture is captured with the illumination in setting position (ii), i.e. with the elements 3" switched on and the diodes 2 activated. In this picture only information about the areas around the found eyes is forwarded to the unit 6. Reflections and thereby images of eyes in the picture are determined. Thereupon, in a block 79 again the procedure according to FIG. 6 is executed to determine which eye is which one. In the next step 81 it is decided whether two eyes have been found in the picture. If it is true case, in a block 83 a calculation of the point observed by the eyes is performed in the unit 6. Then a block 85 is executed in which again a picture is captured with the illumination in light setting position (i), i.e. with only the elements 3' switched on. For the captured image only information for areas around found eyes is transmitted to the unit 6. From the restricted pictorial information pupils and reflections of the light source are determined in the same way as in step 71. Then in a block 87 again the procedure according to FIG. 6 is executed to determine which eye is which one. In the next step 89 it is decided whether two eyes have been found in the picture. If it is true, in a block 91 a calculation of the point observed or gazed at by the eyes is executed in the same way as in block 83. Thereupon in a block 93 it is decided whether the four last pictures captured were captured with the illumination in light setting position (ii). If it is not true, the block 85 is again executed, and otherwise block 77. If it is determined in any of the blocks 75, 81 and 89 that two eyes have not been found, the block 71 is again executed.

While specific embodiments of the invention have been illustrated and described herein, it is realized that numerous additional advantages, modifications and changes will readily occur to those skilled in the art. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents. It is therefore to be understood that the appended claims are intended to cover all such modifications and changes as fall within a true spirit and scope of the invention.

The invention claimed is:

1. An eye detection installation comprising:
one or more light sources for emitting light in directions toward the head of a user,
a detector for receiving light from the head of a user and to repeatedly capture pictures thereof, the detector having a light sensitive surface comprising a plurality of picture elements, and
an evaluation unit connected to the detector for determining the position and/or gaze direction of an eye, the evaluation unit being arranged to determine, in a picture captured by the detector, an area in which an image of an eye or images of eyes is/are located, and, after determining the area, to control the detector to forward to the evaluation unit information about successive or following pictures that only corresponds to the determined area of the image captured by the detectors,
the detector only reading out information from a portion of the detector's surface that corresponds to the determined area, and thereby, data that are then to be forwarded to the evaluation unit, the determined area representing less than all the picture elements of the light sensitive surface.

2. An eye detection installation comprising:
one or more light sources for emitting light in directions toward the head of a user,
a detector for receiving light from the head of a user and to repeatedly capture pictures thereof, and
an evaluation unit connected to the detector for determining the position and/or gaze direction of an eye, the evaluation unit being arranged:
to determine, in a picture captured by the detector, an area in which an image of an eye or images of eyes is/are located,
after determining the area, to control the detector to forward to the evaluation unit information about successive or following pictures that only corresponds to the determined area of the image captured by the detector,
to decide, in a current picture captured by the detector, whether the picture contains images of the two eyes of a user,
in a case where the evaluation unit decides that an image of only one eye exists in the current picture, to determine that the one eye is the same eye that has an image within a previously captured picture, provided that the image of the eye has a position in the current picture that is sufficiently close to the position of the image of the eye in the previously captured picture, and
in the case where the evaluation unit decides that an image of only one eye exists in the current picture, the position of the image of the eye in the current picture does not correspond to or is sufficiently close to the position of any eye in one or more previously captured pictures, and the position of the image of the eye in the current picture is such that the lateral distance from one edge of the current picture is smaller than, but the lateral distance from the other edge is larger than, a distance that corresponds to the distance between the user's eyes, to take the eye, an image of which exists in the current picture, to be the eye that means that an image of the other eye of the user would be located outside the current picture.

3. An eye detection installation comprising:
one or more light sources for emitting light in directions towards the head of a user,
a detector for receiving light from the head of a user and to repeatedly capture pictures thereof, and
an evaluation unit connected to the detector to determine the position and/or gaze direction of an eye, the evaluation unit being arranged:
to determine, in a current picture captured by the detector, whether the picture contains images of the two eyes of a user,
to determine in the case where the evaluation unit decides that an image of only one eye exists in the current picture that the one eye is the same eye, an image of which exists in a previously captured picture, provided that the image of the eye has a position in the current picture that is sufficiently close to the position of the image of the eye of the previously captured image, and
in the case where the evaluation unit decides that an image of only one eye exists in the current picture, that the position of the image of the eye in the current picture does not correspond to or is sufficiently close to the position of any eye in one or more previously captured pictures and that the position of the image of the eye in the current picture is such that the lateral distance from one edge of the current picture smaller than but the lateral distance from the other edge is larger than a distance corresponding to the distance between the eyes of the user, to take that eye, an image of which exists in the current picture, to be the eye that means that an image of the other eye of the user would be located outside the current picture.

4. The eye detection installation according to claim 1, wherein in the case where the evaluation unit cannot from the forwarded information execute the determination, the evaluation unit is arranged to control the detector to forward for the next picture information about a larger portion of picture elements of the light sensitive surface around the previously determined area.

5. The eye detection installation according to claim 1, wherein the evaluation unit is arranged:
to decide in the determined area representing less than all the picture elements of the light sensitive surface captured by the detector whether the picture contains images of the two eyes of a user, and
in the case where the evaluation unit decides that an image of only one eye exists in the the determined area representing less than all the picture elements of the light sensitive surface, to determine that this eye has a position in said determined area that is sufficiently close to the position of the image of the eye in the previously captured image.

6. The eye detection installation according to claim 5, wherein in the case where the evaluation unit decides that an image of only one eye exists in the the determined area representing less than all the picture elements of the light sensitive surface, the position of the image of the eye in said determined area does not correspond to or is sufficiently close to the position of any eye in one or more previously captured pictures, and the position of the image of the eye in said determined area is such that the lateral distance from one edge of said determined area is smaller than but the lateral distance from the other edge is larger than a distance that corresponds to the distance between the user's eyes, the evaluation unit is arranged to take the eye, an image of which exists in the said determined area, to be the eye that means that an image of the other eye of the user would be located outside said determined area.

7. The eye detection installation according to claim 1, wherein
   at least two light sources are provided and placed at a distance from each other for emitting at least two light beams to be reflected from the cornea of an eye of a user, and
   the evaluation unit is arranged to use in a captured image the positions of the images of the reflections of the light sources to determine the location of the eye in relation to the detector.

8. The eye detection installation according to claim 7, wherein the evaluation unit is arranged to determine the distance between images of the reflections of the light sources in a captured picture to determine there from the distance to the eye from the detector.

9. The eye detection installation according to claim 7, wherein at least three light sources are provided in a definite pattern, the evaluation unit arranged to determine the positions of images of the reflections of the light sources and to use all the determined positions to determine the location of the eye in relation to the detector.

10. The eye detection installation according to claim 7, wherein the light sources are divided into groups, a first group of which is arranged to emit light suited to determine, from pictures captured with illumination from only this group, the gaze direction of the eye, and a second group of which is arranged to emit light suited to determine, from pictures captured with illumination from only this group, the distance of the eye from the detector, the control unit arranged to switch either one of or both these groups on in capturing each picture.

11. The eye detection installation according to claim 7, wherein one of the light sources is arranged to emit light in a light beam coaxial with the optical axis of the detector.

12. The eye detection installation according to claim 7, wherein the light sources are divided in two groups, a first group of which is arranged to emit light that causes a bright eye effect and hence is suited to determine, from images captured with illumination from only this group, the gaze direction of the eye, and a second group of which is arranged to emit light suited to determine, from pictures captured with illumination from only this group, the distance of the eye from the detector, the control unit being arranged to activate either one or both of these groups in captured in each picture.

* * * * *